United States Patent
Zanghellini et al.

(10) Patent No.: US 6,635,691 B2
(45) Date of Patent: Oct. 21, 2003

(54) DENTAL MATERIAL CONTAINING A COMPONENT WHICH CONTRACTS DURING THERMAL TREATMENT

(75) Inventors: Gerhard Zanghellini, Schaan (LI); Konrad Hagenbuch, Grabs (CH)

(73) Assignee: Ivoclar Vivadent AG (LI)

(*) Notice: Subject to any disclaimer, the term of this patent is extended or adjusted under 35 U.S.C. 154(b) by 0 days.

(21) Appl. No.: 09/933,025

(22) Filed: Aug. 20, 2001

(65) Prior Publication Data
US 2002/0040075 A1 Apr. 4, 2002

Related U.S. Application Data
(60) Provisional application No. 60/263,371, filed on Jan. 23, 2001.

(30) Foreign Application Priority Data
Aug. 21, 2000 (DE) .......................................... 100 40 772

(51) Int. Cl.[7] .............................. C08F 2/46; A61C 5/08
(52) U.S. Cl. ...................... 523/105; 523/115; 523/116; 433/222.1; 433/226; 433/229; 428/34.9; 428/35.7; 106/35; 522/100; 522/90; 522/96; 522/170; 522/181; 522/81; 522/71; 522/74; 522/77; 522/79; 522/80
(58) Field of Search ................................ 523/105, 115, 523/116; 433/222.1, 226, 229; 428/34.9, 35.7; 106/35; 522/100, 90, 96, 170, 181, 70, 71, 74, 80, 77, 79, 81

(56) References Cited

U.S. PATENT DOCUMENTS

| | | | | |
|---|---|---|---|---|
| 4,512,743 A | * | 4/1985 | Santucci et al. | 433/217 |
| 4,909,736 A | * | 3/1990 | Ritter | 428/182 |
| 5,089,306 A | * | 2/1992 | Grossman et al. | 428/35.1 |
| 5,110,513 A | * | 5/1992 | Puvilland | 264/19 |
| 5,266,609 A | * | 11/1993 | Hall et al. | 523/116 |
| 5,382,160 A | * | 1/1995 | Shemet | 433/39 |
| 5,444,104 A | | 8/1995 | Waknine | |
| 5,698,020 A | * | 12/1997 | Salz et al. | 106/35 |

FOREIGN PATENT DOCUMENTS

| | | |
|---|---|---|
| DE | 3632868 A1 | 10/1987 |
| DE | 4238470 C2 | 1/1995 |
| EP | 0 872 218 A2 | 10/1998 |
| WO | WO 95/08300 | 3/1995 |

* cited by examiner

Primary Examiner—James J. Seidleck
Assistant Examiner—Sanza L. McClendon
(74) Attorney, Agent, or Firm—Nixon Peabody LLP

(57) ABSTRACT

The invention relates to dental materials which contain filler and a polymerizable matrix and are characterized in that they additionally have a component which contracts during thermal treatment.

38 Claims, 2 Drawing Sheets

DENTAL MATERIAL CONTAINING A COMPONENT WHICH CONTRACTS DURING THERMAL TREATMENT

This application claims the benefit of U.S. Provisional Patent Application No. 60/263,371, filed Jan. 23, 2001, which is herein incorporated by reference in its entirety.

The invention relates to dental materials which, in addition to a filler and a polymerizable matrix, contain a component which contracts during thermal treatment.

Dental materials based on plastics contain in general one or more fillers in addition to a polymerizable matrix. The fillers serve to reduce the polymerization shrinkage and to improve the mechanical properties of the cured materials. Fibre composites contain fibrous fillers such as fibre mats or fibre bundles, which are impregnated with the organic polymer matrix. For reasons of stability, it is advantageous to select the filler content as high as possible. This has however the disadvantage that the rigidity of the uncured material is increased and thus its shaping made difficult.

WO95/08300 discloses a process for preparing dental restorations from fibre composites in which fibre mats saturated with polymer matrix are applied to a tooth cast, matched to the cast in a thermoforming process and then cured. The frame obtained in this way can be further processed e.g. by applying facing material.

EP 0 872 218 A2 discloses a process for preparing fibre-reinforced dental restorations, in which the fibre content of the uncured starting material is increased during deep-drawing by expressing excess matrix material. The process necessitates the use of specially designed moulds.

The known deep-drawing processes have the disadvantage that the compaction forces do not act homogenously on the material from all sides simultaneously and no uniform compaction of the materials is achieved.

The object of the invention is the provision of dental material which can be compacted uniformly without special auxiliary agents.

Figure 1:
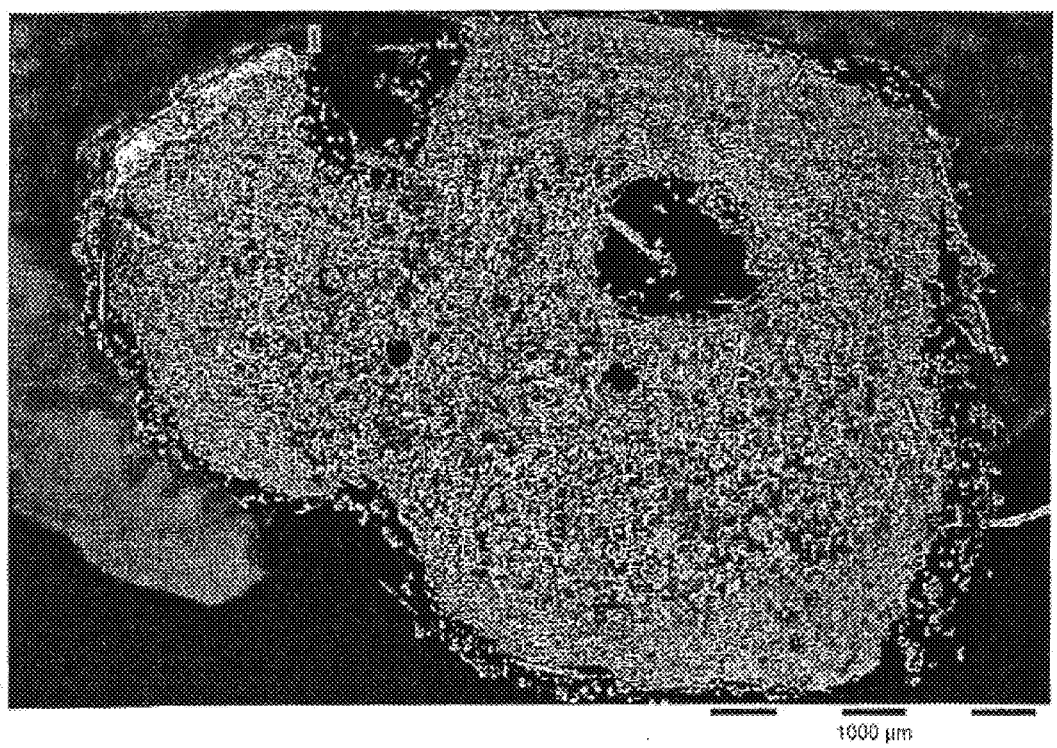
FIG. 1 is an electron microscope picture of a cross-section through a rod-shaped composite material.

This object is achieved by dental materials which, in addition to filler and a polymerizable matrix, contain a component which contracts during thermal treatment. This component is also called shrinkage material in the following.

Preferred components which contract during thermal treatment are so-called shrink films and shrink tubes i.e. plastics films or plastics tubes which contract during heating. These are mostly thermoplastics which are uni- or bi-dimensionally stretched during the course of their production and then contract again on heating.

Suitable shrink films and shrink tubes are commercially available. In particular, shrinkage materials based on polytetrafluoroethylene (PTFE), polyvinylidene fluorides, such as vinylidene fluoride hexafluoropropylene, polyolefins, such as polyethylene and radiation-cross-linked polyolefins, polyethylene terephthalate (PETP), and polyvinyl chloride (PVC) have proved themselves for the preparation of dental materials. Single-layered materials are preferred.

The shrinkage temperature of these materials is normally in the range from 80 to 330° C. Preferred materials are those which contract in the temperature range from 80 to 160° C.

Materials preferred according to the invention have a shrinkage rate in the range from 1.3:1 to 5:1. Materials with a shrinkage rate of 3.5:1 to 4.5:1 and in particular approximately 4:1 are particularly preferred. Shrinkage rates are, if not otherwise stated, measured at a temperature of 150° C.

Materials which shrink only uni-dimensionally are preferred. In the case of tubes, the shrinkage preferably takes place in radial direction whilst the length of the tube remains essentially unchanged. The shrinkage rate in radial direction indicates the ratio of the internal diameter of the non-shrunk tube to the internal diameter of the shrunk tube. At a shrinkage rate of e.g. 4, the internal diameter before the shrinkage is four times greater than afterwards.

Furthermore, transparent shrinkage materials are preferred, as these permit a photochemical curing of the polymerizable material and in addition allow the preparation of dental restorations with a natural appearance.

Polymerizable monomers, oligomers, polymers and prepolymers as well as mixtures of these substances are suitable as polymerizable matrix. Preferred monomers are ionically and/or radically polymerizable mono- or multi-functional monomers, in particular mono(meth)acrylates, such as methyl-, ethyl-, butyl-, benzyl-, furfuryl- or phenyl(meth) acrylate, multi-functional acrylates and methacrylates such as for example bisphenol-(A)-di(meth)acrylate, bis-GMA (an addition product of methacrylic acid and bisphenol-A-diglycidyl ether), UDMA (an addition product of 2-hydroxyethyl methacrylate and 2,2,4-hexamethylene diisocyanate), di-, tri- and tetraethylene glycol di(meth) acrylate, decanediol di(meth)acrylate, trimethylolpropane tri (meth) acrylate, pentaerythritol tetra(meth) acrylate and butanediol di(meth)acrylate, 1,10-decanediol di(meth)-acrylate or 1,12-dodecanediol di(meth)acrylate.

Bisphenol-A-derivates such as bisphenol-A-glycidyl-dimethacrylate (bis-GMA), urethane dimethacrylate (UDMA), triethylene glycol dimethacrylate (TEDMA) and mixtures thereof are preferred among the aromatic dimethacrylate resins.

Other preferred polymerizable materials are polycarbonate-di (meth)acrylates, in particular the condensation product of a hydroxyalkyl methacrylate, preferably 2-hydroxyethyl methacrylate, and a bis(chloroformate), preferably triethylene glycol bis(chloroformate), polycarbonate-tri- or -tetra(meth)acrylates, urethane-di-, tri-, tetra(meth)acrylates and mixtures thereof. Monomers of this type are described in DE 36 32 868 A1 and U.S. Pat. No. 5,444,104.

According to the invention, resin based on bis-GMA can also preferably be used which was modified by copolymerization with materials having low molecular weight, such as bisphenolglycidyl dimethacrylate (BIS-MA), bisphenol-ethyl methacrylate (BIS-EMA), bisphenol propylmethacrylate (BIS-PMA), ethylene glycol dimethacrylate (EGDMA), diethylene glycol dimethacrylate (DEGDMA), triethylene glycol dimethacrylate (TEGDMA), triethylene glycol methacrylate (TEGMA), methyl methacrylate (MMA), and polyurethane fluoromethacrylate (PFUMA).

A polymerizable matrix based on a mixture of bis-GMA, decanediol dimethacrylate (DDDMA), triethylene glycol dimethacrylate (TEGDMA) and urethane dimethacrylate (UDMA) is particularly preferred. A particularly preferred polymerizable matrix contains 65 to 75 wt.-% bis-GMA, 10 to 20 wt.-% triethylene glycol dimethacrylate and 5 to 15 wt.-% highly-dispersed silicon dioxide (relative to the mass of the matrix without fibrous fillers and without shrinkage material).

The matrix preferably contains thermal and/or photoinitiators to initiate the radical polymerization.

Preferred initiators for the thermal curing are peroxides, such as for example dibenzoyl peroxide, dilauryl peroxide, tert.-butylperoctoate and tert.-butylperbenzoate as well as azo-bisisobutyroethyl ester, benzpinacol and 2,2-dimethylbenzpinacol.

Preferred photoinitiators are benzophenone and benzoin as well as their derivatives, α-diketones and their derivatives, such as for example 9,10-phenanthrenequinone, diacetyl and 4,4-dichlorobenzil. Particularly preferred photoinitiators are camphor quinone and 2,2-methoxy-2-phenyl-acetophenone and in particular, combinations of α-diketones with amines as reduction agents, such as for example N-cyanoethyl-N-methylaniline, 4-(N,N-dimethylamino)-benzoic acid ester, N,N-dimethylaminoethyl methacrylate, N,N-dimethylsym.-xylidine or triethanolamine. In addition, acylphosphines, such as for example 2,4,6-trimethylbenzoyldiphenyl- or bis-(2,6-dichloro-benzoyl)-4-N-propylphenylphosphinic oxide, are suitable as photoinitiators.

Organic and inorganic fibrous materials, in particular fibre mats and/or uniaxially oriented fibre bundles, are preferred as fillers. The fibre bundles can be wrapped or braided with fibres to further increase the mechanical strength. The material can contain one or more fibre bundles.

Preferred fibres are glass fibres, aramid fibres, carbon fibres and polyethylene fibres (PE-fibres) and their combinations. Preferred particulate fillers are amorphous spherical materials based on mixed oxides of $SiO_2$, $ZrO_2$ and/or $TiO_2$ (DE 40 29 230 Al), microfine fillers such as pyrogenic silica or precipitation silica as well as macro- (particle size of 5 $\mu$m to 200 $\mu$m) or mini-fillers (particle size of 0.5 to 5 $\mu$m), such as quartz, glass ceramic or glass powder with an average particle size of 0.5 $\mu$m to 5 $\mu$m as well as x-ray opaque filler, such as ytterbium trifluoride.

Combinations of fibrous and particulate fillers are possible.

The mixtures can also contain further additives such as colorants (pigments and dyes), stabilizers, aromatic substances, microbiocidal active ingredients, plasticizers and/or UV absorbers.

Suitable fibre composites, i.e. combinations of organic matrix, fibrous filler, optionally particulate filler, auxiliary agents and additives are described in WO95/08300.

Preferred fibre composites for use with shrinkage materials contain 7 to 94 wt.-% fibrous filler and 6 to 93 wt.-% polymerizable matrix. Particularly preferred are materials which contain 28 to 82 wt.-% and in particular 35 to 65 wt.-% fibrous fillers.

The proportion of non-fibrous fillers preferably lies in the range from 0 to 30 wt.-%, in particular 2 to 15 wt.-% and particularly preferred in the range from 3.5 to 5.5 wt.-%. According to a quite particularly preferred version, the material contains 3.5 to 5.5 wt.-% highly-dispersed silica as additional filler.

Initiators and optionally accelerators are used preferably in a quantity of 0.01 to 3.0 wt.-% each, particularly preferably in a quantity of 0.05 to 1.0 wt.-% each relative to the mass of matrix material. The overall quantity of catalysts and stabilizers is preferably 0.3 to 0.5 wt.-% each based on the overall mass of the fibre composite.

Other additives, such as e.g. pigments, are normally used in a quantity of less than 0.1 wt.-%.

Fibrous and non-fibrous inorganic fillers are preferably made water-repellent before being incorporated into the matrix, particularly preferably silanized, i.e. treated with an organic silicon compound such as an aryloxysilane, alkoxysilane and/or a halogensilane such as (meth) acryloylalkoxysilane.

All the percentages named above and in the following relate, if not otherwise stated, to the mass of the fibre composite without the shrinkage component.

The composition of particularly preferred fibre composites is stated in the following by way of example (all figures are in wt.-%):

| Component | Material No. 1 | Material No. 2 | Material No. 3 |
|---|---|---|---|
| Bis-GMA | 38.7 | 24.6 | 35.3 |
| DDDMA | 0.5 | 0.3 | 0.4 |
| TEDMA | 9.7 | 6.2 | 8.8 |
| Highly-dispersed silica | 5.5 | 3.5 | 5.0 |
| Catalysts and stabilizers | ≦0.5 | ≦0.3 | ≦0.4 |
| Pigments | ≦0.1 | ≦0.1 | ≦0.1 |
| Glass fibres | 45.0 | 65.0 | 50.0 |

According to a preferred version, the component which contracts when exposed to heat is shaped like a tube. This is filled with filler, preferably a fibrous filler, and matrix. When the tube is heated, its inner and outer diameter decreases, whereby the fibres are uniformly Compacted in the matrix and excess matrix material is expressed from the tube at the ends of the tubes. With long tubes, the use of perforated tubes can be advantageous in order to facilitate the escape of the matrix material. This compaction leads to an increase in the fibre content and thus the strength of the dental material.

In general, the fibre content can be increased one- to four-fold. The degree of compaction can be so controlled via the shrinkage ratio of the shrinkage material that the desired mechanical properties are achieved.

To determine the compaction ratio, cross-sections of cured composite material with and without shrinkage material are produced and the ratio of the areas covered by fibres and matrix material are ascertained in each case. The compaction corresponds to the quotients from the area ratio of fibre to matrix with shrinkage material and the area ratio of fibre to matrix without shrinkage material. If only inorganic fibres are used, such as e.g. glass fibres, the compaction or the fibre content can also be ascertained via the ash content.

Figure 2:
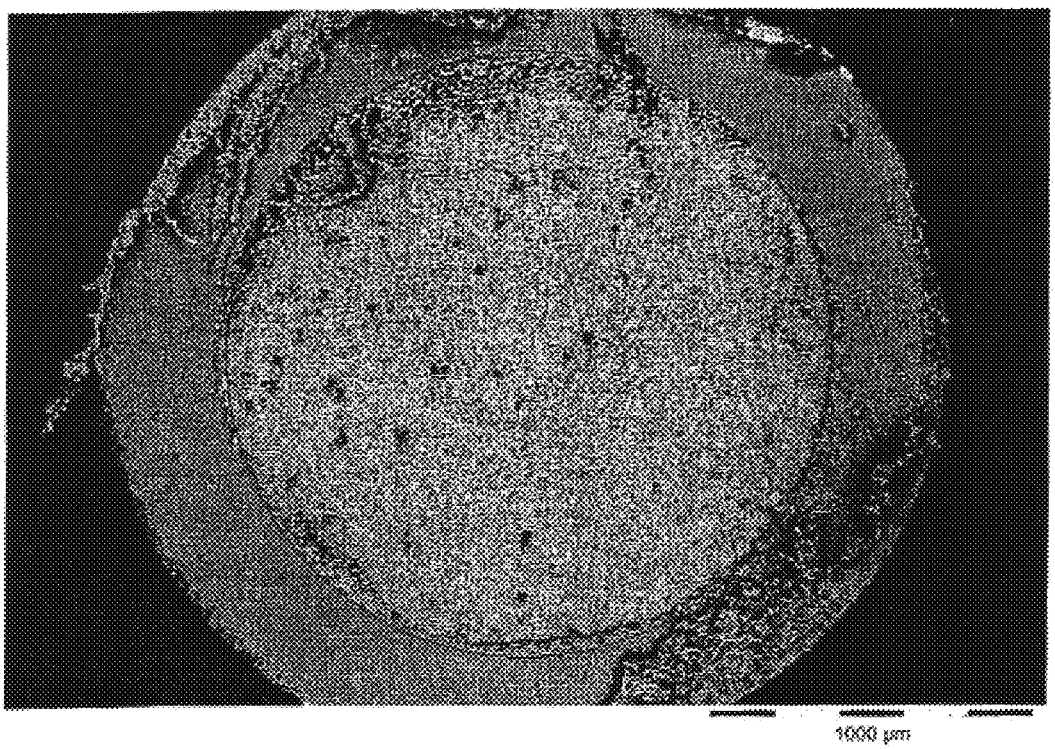
FIG. 2 is an electron microscope picture of a cross-section through a composite material which is contained in a shrink tube.

FIG. 1 shows an electron microscope picture of a cross-section through a rod-shaped composite material which was cured without shrinkage material, FIG. 2 the picture of a cross-section through a second composite material which is contained in a shrink tube. In both cases, the section was cut perpendicular to the fibre direction and to the longitudinal axis of the material. The compositions of the composite materials before curing and compaction were identical and correspond in both cases to material no. 2 described above.

A visual comparison of the figures already shows that the fibre density of the material with shrink tube is clearly higher than the material without shrink tube. In addition, the latter contains large air inclusions.

A measurement of the cross-section surfaces without and with shrink tube produced values of 4.44 mm$^2$ (without taking the large air inclusion into account) and 2.81 mm$^2$.

Figure 3:
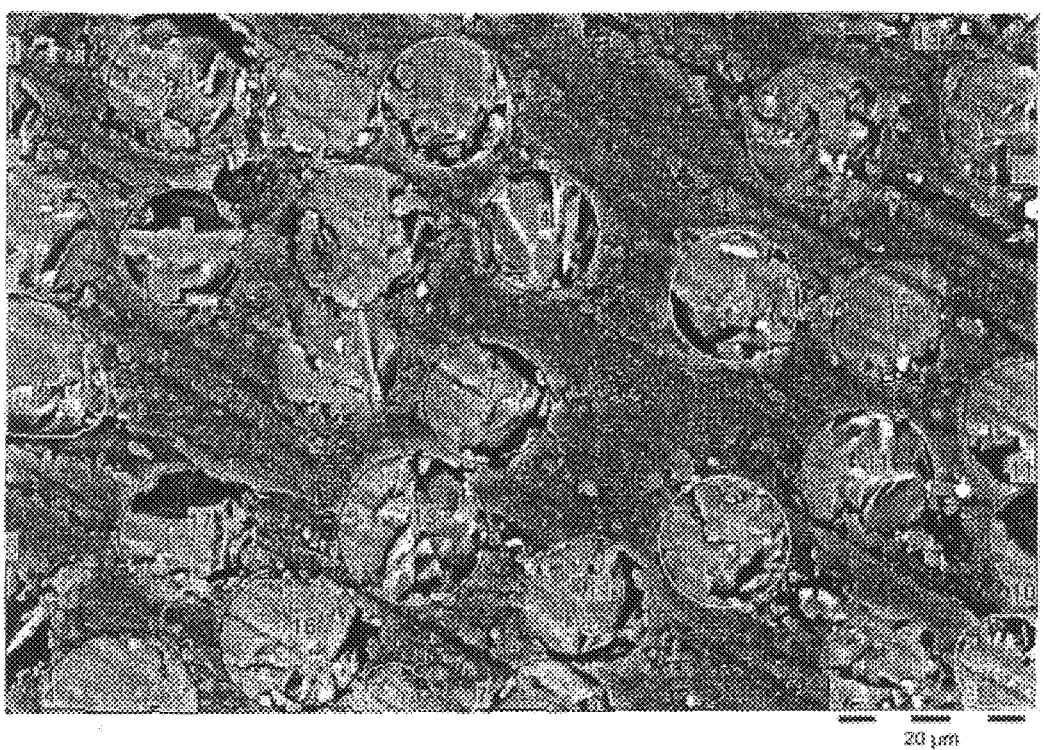
FIG. 3 is an electron microscope picture of the cross-section shown in FIG. 1 at a greater magnification and FIG. 4 is an electron microscope picture of the cross-section shown in FIG. 2 at a greater magnification.
Figure 4:
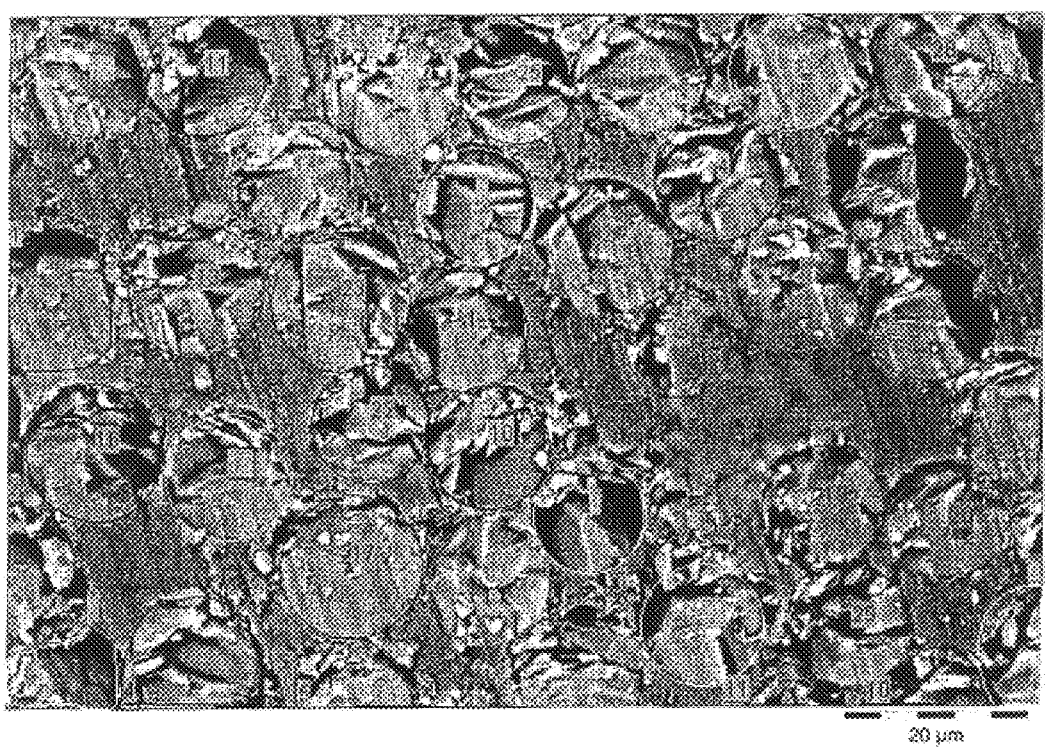

FIGS. 3 and 4 show parts of the same cross-sections at a greater magnification. Fibres and matrix can be clearly differentiated. In FIG. 3 (material without shrink tube), the area occupied by the fibres is 3863 $\mu$m$^2$, the area of the matrix 4573 $\mu$m$^2$ and the overall area 8436 $\mu$m$^2$. The area ratio of fibres to matrix is accordingly 0.84.

In FIG. 4 (material with shrink tube), the area occupied by the fibres is 5385 $\mu$m$^2$, the area of the matrix 3237 $\mu$m$^2$ and the total surface area 8622 $\mu$m$^2$. The surface area ratio of fibres to matrix is 1.66. This results in a compaction of 1.66:0.84=1.98.

According to a further preferred version, uniaxially oriented fibres are encased in a tube made from a woven or knitted fibre fabric and this combination is then enclosed by a component which contracts during thermal treatment. The compaction which occurs during heating improves the orientation of the fibres and thus the transverse tensile strength, compressive strength and torsional strength of the rod.

Tube- or rod-shaped components are suitable in particular for the production of fibre-reinforced dental bridge frames. The spatial measurements of the components are matched to the production of dental restorations. Rod-shaped materials with a length of 10 to 160 mm and a diameter of 2 to 4 mm (measured without shrinkage material) are preferred. The materials preferably have a circular cross-section. They are characterized in that the fibre bundle impregnated with organic matrix can easily be processed from outside while dry and thus by hand without risk of soiling and without the risk of contaminating the fibre bundles.

The materials according to the invention are shaped for example using casts, such as casts with detachable segments made from plaster and then heated. In the process, the component, which contracts during thermal treatment, shrinks and thus effects a compaction of the dental material. The material is then cured, preferably by radical polymerization.

The shrinkage material is preferably removed after polymerization and the remaining, cured composite material is processed further, for example faced with suitable materials.

It is however also conceivable that the shrinkage material is firmly bonded to the matrix via polymerizable groups during polymerization.

The compaction of fibre composites can also be achieved by using shrinkage strips. A strip of the material contracting during thermal treatment is wrapped round the fibre composite, optionally together with the cast and preferably after shaping, and this is then heated. The strip shrinks and compacts the wrapped material. Complicated structures can also be homogenously compacted by using shrinkage strips. After the polymerization of the matrix, which can take place during or after heating, the strips are removed from the dental restoration and the latter optionally further processed, for example faced or crowned. In the case of shrinkage strips, the overlapping points of the strips serve as outlets for the monomer.

The strips preferably have a width of 5 to 100 mm, particularly preferably 10 to 30 mm. The thickness of the strips is variable and is typically about 0.4 mm. The shrinkage rate of the strips, measured in longitudinal direction, is preferably 1.3:1 to 4:1.

For the further processing of the cured materials, e.g. for the application of facing materials, it is generally necessary to roughen the surface of the fibre composite. This step involves additional outlay. For this reason, a so-called tear-off fabric is applied to the dental restoration first before the shrinkage material. By tear-off fabrics are meant materials which can be removed (torn off) from the cured fibre composite after polymerization and in the process leave a clean rough surface behind. The fibre composite can be further processed after the tear-off fabric is removed without additional roughening of the surface.

According to a further version of the invention, caps of shrinkage material are filled with polymerizable composite material and then matched to a cast, such as for example a tooth stump, by shrinkage. Size and shape of the caps are matched to the use with teeth and tooth stumps. The polymerizable material is then cured, the shrinkage material is optionally removed and the cured moulding is optionally further processed, for example by applying facing material. In this way, e.g. dental crowns and bridge piers can be prepared for permanent and temporary use.

The preparation of a crown is described in the following in more detail. The tooth to be restored is ground to a stump in a manner known per se. A negative mould is prepared from the stump with impression materials such as for example alginate, polyether or silicon, and this is then cast with a modelling material such as plaster or epoxy resin. In this way, a positive cast is obtained which is insulated e.g. with an alginate solution (in the case of a plaster cast), or a wax solution (in the case of an epoxy cast). A small cap made from a shrinkage material, which is filled with polymerizable material, is then applied to the insulated cast stump. The cap is fitted onto the stump in such a way that it covers this. The cap is shrunk by heating and the polymerizable material matched to the stump and simultaneously compacted. The material is then cured by light or further heating and the cured material is made into the finished crown according to the usual dentistry methods, e.g. by applying a suitable facing material. For this, the surface of the crown blank is optionally roughened and the facing material applied to the roughened surface. As a rule, the application takes place in two or more layers, each of the individual layers being cured after the application. After the last layer has been applied, the crown is subjected to final curing, polished, cleaned and fitted to the patient by the dentist.

To manufacture a bridge, filling cavities are distally or mesially prepared by the dentist with suitable instruments in a manner known per se in the two teeth adjacent to the gap in the teeth and then a positive cast is made of the mouth situation as described above and this is insulated. The insulation prevents the frame material from sticking to the cast. Then e.g. a rod-shaped, fibre-reinforced composite material, which is preferably contained in a shrink tube, is cut to a length which corresponds to the distance between the two prepared cavities. This strand is then introduced into the cavities so that it spans the gap between the teeth. To prevent the strand deforming during heating, it can be fixed at both ends, e.g. by curing matrix monomer which emerges there through brief irradiation with an optical conductor. Alternatively or simultaneously, the strand can be supported with silicon material so that that it cannot bend downwards. Support is required above all if large gaps (larger than approx. 6 mm) must be spanned. Subsequently, the material is heated to shrinkage temperature by a heat source, e.g. by a hot-air blower or an IR radiator. After shrinking, the strand is cured with a light source, e.g. Heliolux or Targis Power, the shrink tube is removed and the frame is faced with a facing material in the usual way. To remove the shrink tube, this is preferably cut open and then peeled off.

What is claimed is:

1. Dental material comprising a filler, a polymerizable matrix, and in addition to the filler and the polymerizable matrix, a component which contracts during thermal treatment, wherein the polymerizable matrix comprises 65 to 75 wt.-% bis-GMA, 10 to 20 wt.-% triethylene glycol dimethacrylate and 5 to 15 wt.-% of highly-dispersed silicon dioxide.

2. Dental material comprising a thermally contractable tube filled with material comprising a polymerizable matrix and a filler.

3. Dental material according to claim 2, wherein said filler comprises fibrous filler.

4. Dental material according to claim 3, wherein said fibrous filler comprises glass fibres, aramid fibres, carbon fibres, polyethylene fibres, or combinations thereof.

5. Dental material according to claim 3, wherein the fibrous filler contains one or more uniaxially oriented fibre bundles.

6. Dental material according to claim 2, wherein the thermally contractable tube can be removed after polymerization of the matrix.

7. Dental material according to claim 2, wherein the thermally contractable tube has a shrinkage rate of from 1.3:1 to 5:1.

8. Dental material according to claim 2, wherein the thermally contractable tube is transparent.

9. Dental material according to claim 2, comprising 7 to 94 wt.-% of fibrous filler and 6 to 93 wt.-% of polymerizable matrix relative to the mass of the filler and matrix without the thermally contractable tube.

10. Dental material according to claim 2, comprising 0 to 30 wt.-% of non-fibrous fillers relative to the mass of the filler and matrix without the thermally contractable tube.

11. Dental material according to claim 2, wherein said polymerizable matrix comprises a mixture of bis-GMA, decanediol dimethacrylate (DDMA), triethylene glycol dimethacrylate (TEGDMA) and urethane dimethacrylate (UDMA).

12. Dental material according to claim 2, wherein the polymerizable matrix comprises 65 to 75 wt.-% bis-GMA, 10 to 20 wt.-% triethylene glycol dimethacrylate and 5 to 15 wt.-% of highly-dispersed silicon dioxide.

13. Process for manufacturing a dental bridge, comprising filling a thermally contractable tube with a polymerizable matrix and a filler and subsequently subjecting the tube to a thermal treatment.

14. Process for manufacturing a dental bridge according to claim 13, further comprising curing the dental bridge.

15. Process for manufacturing a dental bridge according to claim 13, further comprising fixing at least one end of the bridge to a curable dental restoration by curing the bridge and dental restoration.

16. Dental material according to claim 1, wherein said filler comprises fibrous filler.

17. Dental material according to claim 16, wherein said fibrous filler comprises glass fibres, aramid fibres, carbon fibres, polyethylene fibres, or combinations thereof.

18. Dental material according to claim 16, wherein the fibrous filler contains one or more uniaxially oriented fibre bundles.

19. Dental material according to claim 1, comprising 7 to 94 wt.-% of fibrous filler and 6 to 93 wt.-% of polymerizable matrix relative to the mass of the filler and matrix without the component which contracts during thermal treatment.

20. Dental material according to claim 1, comprising 0 to 30 wt.-% of non-fibrous fillers relative to the mass of the filler and matrix without the component which contracts during thermal treatment.

21. A method for increasing the fibre content of a cured dental material as compared to the uncured dental material, comprising providing a dental material comprising a polymerizable matrix and a fibrous filler; surrounding at least a portion of the dental material with a component that contracts during thermal treatment; and subsequently subjecting the dental material to a thermal treatment, wherein excess matrix material is expressed from the surrounded portion of the dental material.

22. The method according to claim 21, further comprising curing the compacted dental material.

23. The method according to claim 22, wherein said curing is obtained by radical polymerization.

24. The method according to claim 21, wherein said fibrous filler comprises glass fibres, aramid fibres, carbon fibres, polyethylene fibres, or combinations thereof.

25. The method according to claim 24, wherein the fibrous filler contains one or more uniaxially oriented fibre bundles.

26. The method according to claim 21, further comprising removing the component that contracts during thermal treatment after polymerization of the matrix.

27. The method according to claim 21, wherein the component that contracts during thermal treatment has a shrinkage rate of from 1.3:1 to 5:1.

28. The method according to claim 21, wherein the component that contracts during thermal treatment is transparent.

29. The method according to claim 21, wherein the component that contracts during thermal treatment is shaped like a tube.

30. The method according to claim 21, wherein the component that contracts during thermal treatment is shaped like a cap.

31. The method according to claim 21, wherein the component that contracts during thermal treatment is shaped like a film or a strip.

32. The method according to claim 21, wherein the dental material comprises 7 to 94 wt.-% of fibrous filler and 6 to 93 wt.-% of polymerizable matrix relative to the mass of the filler and matrix without the component which contracts during thermal treatment.

33. The method according to claim 21, wherein the dental material comprises 0 to 30 wt.-% of non-fibrous fillers relative to the mass of the filler and matrix without the component which contracts during thermal treatment.

34. The method according to claim 21, wherein the polymerizable matrix comprises a mixture of bis-GMA, decanediol dimethacrylate (DDMA), triethylene glycol dimethacrylate (TEGDMA) and urethane dimethacrylate (UDMA).

35. The method according to claim 21, wherein the polymerizable matrix comprises 65 to 75 wt.-% bis-GMA, 10 to 20 wt.-% triethylene glycol dimethacrylate and 5 to 15 wt.-% of highly-dispersed silicon dioxide.

36. The method according to claim 21, wherein the dental material is a dental bridge.

37. The method according to claim 36, further comprising curing the dental bridge.

38. The method according to claim 37, further comprising fixing at least one end of the bridge to a curable dental restoration by curing the bridge and dental restoration.

* * * * *